United States Patent
Solis Herrera

(10) Patent No.: US 10,220,021 B2
(45) Date of Patent: Mar. 5, 2019

(54) METHODS FOR TREATING AND PREVENTING OCULAR DISEASES, DISORDERS, AND CONDITIONS WITH MELANIN AND MELANIN ANALOGS, PRECURSORS, AND DERIVATIVES

(71) Applicant: Arturo Solis Herrera, Aguascalientes (MX)

(72) Inventor: Arturo Solis Herrera, Aguascalientes (MX)

(*) Notice: Subject to any disclaimer, the term of this patent is extended or adjusted under 35 U.S.C. 154(b) by 0 days.

(21) Appl. No.: 15/509,532

(22) PCT Filed: Sep. 8, 2015

(86) PCT No.: PCT/IB2015/001570
§ 371 (c)(1),
(2) Date: Mar. 8, 2017

(87) PCT Pub. No.: WO2016/038441
PCT Pub. Date: Mar. 17, 2016

(65) Prior Publication Data
US 2017/0296511 A1    Oct. 19, 2017

Related U.S. Application Data

(60) Provisional application No. 62/048,013, filed on Sep. 9, 2014.

(51) Int. Cl.
| | | |
|---|---|---|
| *A61K 31/407* | (2006.01) | |
| *A61K 31/405* | (2006.01) | |
| *A61K 31/787* | (2006.01) | |
| *A61K 9/00* | (2006.01) | |
| *A61K 9/08* | (2006.01) | |
| *A61P 27/02* | (2006.01) | |

(52) U.S. Cl.
CPC .......... *A61K 31/407* (2013.01); *A61K 9/0019* (2013.01); *A61K 9/0048* (2013.01); *A61K 9/08* (2013.01); *A61K 31/405* (2013.01); *A61K 31/787* (2013.01); *A61P 27/02* (2018.01)

(58) Field of Classification Search
CPC .................................................... A61K 31/407
See application file for complete search history.

(56) References Cited

U.S. PATENT DOCUMENTS

| | | | |
|---|---|---|---|
| 6,773,916 | B1 | 8/2004 | Thiel et al. |
| 8,455,145 | B2 | 6/2013 | Solis Herrera |
| 2002/0128304 | A1 | 9/2002 | D'Amato |
| 2003/0096735 | A1 | 5/2003 | D'Amato |
| 2005/0148516 | A1 | 7/2005 | Taniguchi et al. |
| 2010/0010082 | A1 | 1/2010 | Chong et al. |
| 2012/0270907 | A1 | 10/2012 | Herrera |
| 2013/0109745 | A1 | 5/2013 | Ji et al. |

FOREIGN PATENT DOCUMENTS

| | | |
|---|---|---|
| EP | 1460134 A1 | 9/2004 |
| EP | 2594268 A1 | 5/2013 |
| JP | 2009517396 A | 4/2009 |
| JP | 2013551032 A | 8/2013 |
| KR | 20120008429 A | 1/2012 |
| WO | 1992007580 A1 | 5/1992 |
| WO | 20030060131 A1 | 7/2003 |
| WO | 20070064752 A2 | 6/2007 |
| WO | 2007102724 A2 | 9/2007 |
| WO | 2012008674 A1 | 1/2012 |

OTHER PUBLICATIONS

Int'l Preliminary Report on Patentability dated Mar. 14, 2017 in Int'l Application No. PCT/IB2015/001570.
Int'l Search Report dated Feb. 12, 2016 in Int'l Application No. PCT/IB2015/001570.
Lai et al, "Effect of Melanin on Traumatic Hyphema in Rabbits," Arch. Ophthalmol., vol. 177, No. 6, pp. 789-793 (1999).
Office Action dated Aug. 7, 2017 in CA Application No. 2960583.
Office Action dated Aug. 20, 2018 in KR Application No. 10-2017-7008116.
Office Action dated Sep. 4, 2018 in JP Application No. 2017-532221.
Shinohara, B., "Calcification of Soft Tissues," vol. 49, No. 4, pp. 416-421 (2007) (see English translation of Office Action dated Sep. 4, 2018 in JP Application No. 2017-532221 for brief description of relevance).
Office Action dated Jan. 14, 2018 in KR Application No. 10-2017-7008116.
Office Action dated Jan. 9, 2018 in JP Application No. 2017-532221.
Japanese Journal of Clinical Ophthalmology, vol. 47, No. 4, pp. 582-583 (1993) (see pp. 6 to 7 of the English translation of the Office Action dated Jan. 9, 2018 in JP Application No. 2017-532221).
Office Action dated Mar. 22, 2018 in EP Application No. 15839968.3.
Office Action dated Mar. 29, 2018 in CA Application No. 2,960,583.
Office Action dated Apr. 20, 2018 in RU Application No. 2017111579.
Office Action dated Oct. 7, 2018 in Korean Application No. 10-2017-7008116.

*Primary Examiner* — Zohreh A Fay
(74) *Attorney, Agent, or Firm* — Panitch Schwarze Belisario & Nadel LLP

(57) ABSTRACT

Uses of melanin and its derivatives, analogs, and precursors for the treatment and prevention of ocular diseases, disorders, and conditions, are described. Melanin, or a derivative, analog, or precursor thereof, such as synthetic melanin or natural melanin, is applied to the eye by topical application or injection. Examples of ocular diseases, disorders, and conditions that can be treated or prevented by the methods described herein include hyperemia, leukoplakia, corneal angiogenesis, and corneal keratoconus.

19 Claims, 1 Drawing Sheet

FIG. 1A
Prior to treatment
FIG. 1B
Three and a half months post-treatment
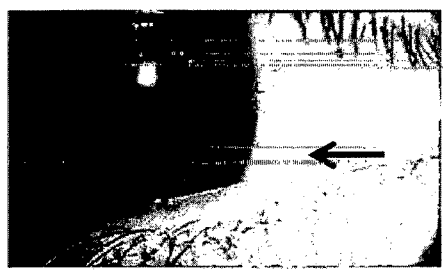
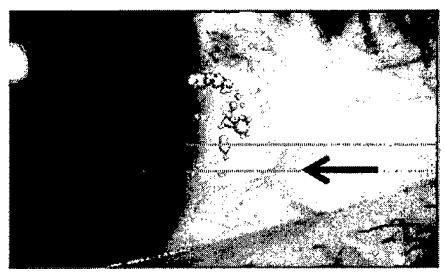
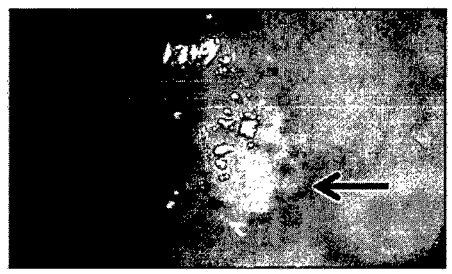
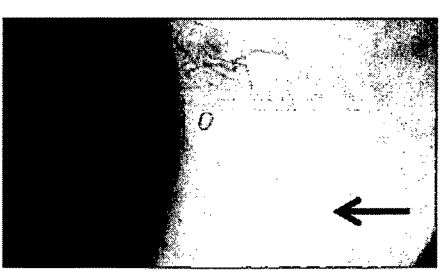

METHODS FOR TREATING AND PREVENTING OCULAR DISEASES, DISORDERS, AND CONDITIONS WITH MELANIN AND MELANIN ANALOGS, PRECURSORS, AND DERIVATIVES

CROSS-REFERENCE TO RELATED APPLICATIONS

This application is a Section 371 of International Application No. PCT/IB2015/001570, filed Sep. 8, 2015, which was published in the English language on Mar. 17, 2016 under International Publication No. WO 2016/038441 A1, which claims priority under 35 U.S.C. § 119(e) to U.S. Provisional Patent Application No. 62/048,013, filed Sep. 9, 2014, and the disclosures of which are herein incorporated by reference.

FIELD OF THE INVENTION

The invention relates to methods of treating and preventing ocular diseases, disorders, and conditions.

BACKGROUND OF THE INVENTION

Melanin is ubiquitous in nature, and is composed of nitrogen, oxygen, hydrogen, and carbon. For many years, melanin had no biological or physiological function attributed to it, other than it being considered a simple sunscreen. Because melanin was able to absorb all wavelengths of electromagnetic energy, but did not seem to emit any energy, it was considered the darkest molecule. This characteristic was unique to melanin, and contradicted thermodynamic laws, because other compounds capable of absorbing energy, particularly pigments, emit at least a portion of the energy absorbed. Thus, the electronic properties of melanin have been the focus of attention for quite some time. However, melanin is one of the most stable compounds known to man, and for a long time, it seemed that melanin was unable to catalyze any chemical reaction, or have any other biological or physiological function.

Recently, the intrinsic ability of melanin to split the water molecule into hydrogen and oxygen upon absorption of electromagnetic energy, such as light energy, has previously been reported in U.S. Pat. No. 8,455,145. It is believed that upon the absorption of electromagnetic energy, such as light energy (visible or invisible), melanin catalyzes the dissociation of water into diatomic hydrogen ($H_2$), diatomic oxygen ($O_2$), and electrons. Although the splitting of water into hydrogen and oxygen consumes energy, the reaction is reversible, and in the reverse process, the reduction of oxygen atoms with diatomic hydrogen reforms water molecules and liberates energy.

It has also recently been demonstrated that nicotine can increase the release or activity of α-melanocyte stimulating hormone (α-MSH) in a subject, which is believed to be efficacious in treating different disorders by inducing "human photosynthesis" in the subject (see, e.g., U.S. Patent Application Publication No. 2012/0270907). Although the mechanism is not fully understood, it is hypothesized that the increased release or activity of α-MSH increases the synthesis of melanin.

Despite the growing knowledge regarding the biological functions of melanin, the therapeutic effects of direct administration of melanin have only been explored in a limited capacity. For example, melanin has been shown to be a simple sunscreen with a low protection factor equivalent to that of a 2% copper sulfate solution. Direct injection of a melanin solution into the anterior chamber of the eye in rabbits was shown to increase both the clearance period of hyphema and the incidence of rebleeds, suggesting that injection of melanin into the eye has a negative effect on the treatment of hyphema. Lai et al. "Effect of Melanin on Traumatic Hyphema in Rabbits" *Arch. Ophthalmol.* (1999) 177, 789-93. However, as far as the inventor is aware, the effect of direct administration of melanin as a therapeutic agent has not yet been fully explored.

BRIEF SUMMARY OF THE INVENTION

It is now discovered that the application of melanin, or an analog, derivative, or precursor thereof, to an eye of a subject has beneficial therapeutic effects in treating and preventing ocular diseases, disorders, and conditions.

The invention relates to methods of treating and preventing ocular diseases, disorders, and conditions by administering to an eye of a subject a composition comprising a therapeutically effective amount of melanin, or a derivative, analog, or precursor thereof.

In one embodiment, the invention provides a method of treating or preventing an ocular disease, disorder, or condition in a subject comprising administering to an eye of the subject a composition comprising a therapeutically effective amount of melanin, or a derivative, analog, or precursor thereof, to treat or prevent the ocular disease, disorder, or condition.

In another embodiment, the invention provides a method of treating an ocular disease, disorder, or condition in a subject comprising topically administering to an eye of the subject in need of the treatment a composition comprising a therapeutically effective amount of melanin or an analog, derivative, or precursor thereof, to treat the ocular disease, disorder, or condition.

In yet another embodiment, the invention provides a method of treating leukoplakia or hyperemia in a human subject comprising topically administering to an eye of the subject in need of the treatment an aqueous composition comprising a therapeutically effective amount of melanin.

In preferred embodiments of the invention, the composition is administered as eye drops.

In other preferred embodiments of the invention, the composition administered to the eye of the subject comprises 1.5% to 10% (w/v) of melanin, or a derivative, analog, or precursor thereof.

In yet other preferred embodiments of the invention, the composition administered to the eye of the subject comprises synthetic melanin or natural melanin.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown in the drawings and described in the following detailed description of the invention. In the drawings:

FIGS. 1A and 1B show photographic images of a right eye of a male patient (age 30) having a small white plaque growing on the surface of the eye (leukoplakia) and hyperemia (redness), before and after treatment with melanin; the images shown from top to bottom are photographs taken of the same view with increasing magnification, and the arrow indicates the position at which the growth of a small white plaque was observed; FIG. 1A: photographic images of the eye prior to treatment with melanin; FIG. 1B: photographic images of the eye three and a half months after topical treatment with a 3% aqueous solution of melanin.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which have been included in the present specification is for the purpose of providing context for the invention. Such discussion is not an admission that any or all of these matters form part of the prior art with respect to any inventions disclosed or claimed.

Unless otherwise defined, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural references unless the context clearly dictates otherwise.

The invention relates to methods of treating and preventing ocular diseases, disorders, and conditions in a subject. According to embodiments of the invention, the method comprises administering to an eye of the subject a composition comprising a therapeutically effective amount of melanin, or a derivative, analog, or precursor thereof to treat the ocular disease, disorder, or condition.

According to embodiments of the invention, a composition used in the methods described herein comprises melanin, or an analog, precursor, or derivative thereof. The composition also optionally comprises one or more pharmaceutically acceptable excipients. In a preferred embodiment, the pH of the composition is near physiological pH, and is about pH 7.0 to pH 7.4.

Derivatives and analogs of melanin that can be used in the methods of the invention include compounds that are derived from, and compounds that are structurally similar to melanin, respectively. Non-limiting examples of derivatives and analogs of melanin include eumelanin, pheomelanin, neuromelanin, sepiomelanins, and alomelanin; aromatic compounds such as dopamine, indole, polyhydroxyindole, humic acid, polyindolequinones, pyrrole black, indole black, benzene black, thiophene black, aniline black, ommochrome black; polyquinones in hydrated form, dopa black, adrenalin black, catechol black, 4-amine catechol black. Precursors of melanin include compounds that can be converted to melanin by chemical, enzymatic, or metabolic reaction, including, but not limited to, phenols, aminophenols, or diphenols, indole polyphenols, quinones, semiquinones or hydroquinones, L-tyrosine, L-dopamine, morpholine, ortho-benzoquinone, dimorpholine, porphyrin black, and pterin black; linear carbon containing compounds such as acetylene black; and carbon building blocks such as fullerenes and graphite.

According to preferred embodiments of the invention, the composition used in the methods of the invention comprises melanin. The melanin used can be natural melanin or synthetic melanin. "Natural melanin" is intended to refer to melanin that is isolated from a natural source, such as a plant or animal. "Synthetic melanin" is intended to refer to melanin that is chemically synthesized.

As used herein, the term "subject" refers to any animal, preferably a mammal, and most preferably a human, to whom has been or will be administered melanin, or an analog, derivative, or precursor thereof. Examples of mammals include humans, cows, dogs, cats, horses, pigs, monkeys, sheep, and rodents. Examples of rodents include rats, mice, rabbits, and guinea pigs. Preferably, the subject is a human.

As used herein, "ocular disease, disorder, or condition" is intended to refer to any disease, disorder, or condition affecting the eye. An ocular disease, disorder, or condition can affect any part of the eye including, but not limited to, the cornea, conjunctiva, eyelid, sclera (white of the eye), retina, or epithelium tissue forming the surface of the eye, or any structure that could be considered as the surface of the eye, including the tear film, Zeiss glands, Moll's Gland, Meibomian gland, etc. The cornea is the transparent tissue at the front of the eye that covers the iris, pupil, and anterior chamber. The cornea is avascular, meaning that it normally has no blood vessels. The cornea also normally has a rounded shape.

According to preferred embodiments of the invention, the ocular disease, disorder, or condition to be treated or prevented affects the surface of the eye or the eyelids.

The etiology of the ocular disease, disorder, or condition to be treated or prevented by the methods of the invention is not limited, and can arise from an infection, allergy or allergic reaction, a degenerative disorder, inflammatory disease, trauma, surgery, radiation, irritation (e.g., from medications or contact lenses), autoimmune disease, or a proliferative disorder. The ocular disease, disorder, or condition can be acute or chronic.

According to embodiments of the invention, the ocular disease, disorder, or condition to be treated or prevented can result in atrophic changes or dystrophic changes to the affected eye. Atrophic changes tend to be more widespread, such that the affected tissue considerably loses its normal capabilities. Dystrophic changes tend to be more localized, such that the affected tissue can have a more normal appearance with only some portions of the tissue being significantly affected. For example, an atrophic disease, disorder, or condition can affect the entire conjunctiva tissue, entire cornea, and/or the entire eyelid, whereas a dystrophic disease, disorder, or condition affects only a portion of the conjunctiva tissue, a portion of the cornea, and/or a portion of the eyelid. Atrophic changes tend to have a minimal inflammatory component, whereas dystrophic changes usually have a significant inflammatory component at least in the affected tissue area.

Non-limiting examples of ocular diseases, disorders, or conditions affecting the cornea include corneal angiogenesis or neovascularization; keratitis (inflammation of the cornea); and corneal ectatic diseases (e.g., corneal keratoconus). Non-limiting examples of ocular diseases, disorders, or conditions affecting the conjunctiva include conjunctivitis. Other examples of ocular diseases, disorders, and conditions include, but are not limited to, hyperemia; chemical burns (e.g., by acid or alkali agent), poisons (natural or synthetic), and insect stings in the eye; diseases accompanied by alteration of the tear film; ulceration (e.g., corneal ulcer); Sjögren's Syndrome; alkali and other chemical burns of the eye; corneal transplant rejection; allergic reactions in the conjunctiva and eyelids; surgery of the eye; inflammation, such as inflammation of the conjunctiva or inflammation of the eyelids; eye infections, including fungal, viral, and bacterial infections; autoimmune diseases; proliferative diseases; leukoplakia (formation of white plaques), vascular diseases (e.g., retinal vascular diseases), and calcification.

As used herein, "hyperemia" generally refers to an increase in blood flow to a tissue, resulting in redness of the tissue experiencing increased blood flow. According to embodiments of the invention, hyperemia refers to increased blood flow to the eye, in chronic and acute form, resulting in increased redness of the eye. Hyperemia of the eye can occur on its own (primary), or it can be a symptom associated with one or more other ocular diseases, disorders, or conditions (secondary). Hyperemia can also be acute or chronic.

As used herein, "angiogenesis" and "neovascularization" refer to the physiological process by which new blood vessels form from preexisting blood vessels. As used herein, the terms "corneal angiogenesis" and "corneal neovascularization" refer to the growth of one or more new blood vessels in the cornea. Because the cornea is avascular, i.e., does not contain any blood vessels, any new blood vessels in the cornea typically arise from the growth of blood vessels from the limbal vascular plexus area of the eye into the cornea.

As used herein, "corneal ectasia" and "corneal ectatic disease" refer to a noninflammatory disease of the cornea characterized by irregularities in the cornea that cause disturbances in vision as a result of astigmatism. Corneal ectasia refers to a group of conditions including keratoconus, pellucid marginal degeneration, keratoglobus, and posterior keratoconus, with the most prevalent, particularly in humans, being keratoconus. According to a preferred embodiment of the invention, a corneal ectatic disease is keratoconus or a variant of keratoconus such as keratoglobus, irregular astigmatism, forme frustre keratoconus, high degree of astigmatism, cicatricial irregular astigmatism, primary ectasia, and secondary ectasia. Corneal ectasia can be inflammatory or non-inflammatory. The term "corneal keratoconus" refers to a disease that affects the structure of the cornea. In corneal keratoconus, the shape of the cornea slowly changes from a rounded shape to a conical shape that bulges outward, forming a protrusion. Corneal keratoconus can also be described as "the loss of shape" of the cornea.

As used herein, the term "conjunctivitis" refers to inflammation of the conjunctiva as the result of an infection or allergic reaction, for example. Conjunctivitis is more commonly referred to as "Pink eye."

As used herein, the term "leukoplakia" refers to a disorder of mucous membranes that manifests as small white plaques or patches on the surface of the mucous membrane. Leukoplakia is often associated with an increased risk of proliferative disorders, e.g., cancer, or uncontrolled cell or tissue growth in the affected area. Leukoplakia most commonly occurs in the part of the eye where one type of epithelium tissue transitions into another type of eplithelium tissue, e.g., in the area the conjunctiva transitions into the corneal epithelium, known as the cornea-scleral limbus.

As used herein, a "therapeutically effective amount" refers to an amount of a therapeutically active ingredient needed to elicit the desired biological or clinical effect. In one embodiment of the invention, a "therapeutically effective amount" is the amount of melanin, or an analog, precursor, or derivative thereof, needed to treat an ocular disease, disorder, or condition. In another embodiment of the invention, a "therapeutically effective amount" is the amount of melanin, or an analog, precursor, or derivative thereof needed to prevent an ocular disease, disorder, or condition.

As used herein, the terms "treat," "treating," and "treatment" refer to administering a therapeutically effective amount of melanin, or an analog, precursor, or derivative thereof in order to reduce, alleviate, or slow the progression or development of an ocular disease, disorder, or condition. In another embodiment, "treat," "treating," and "treatment" refer to reducing, slowing the progression of, or ameliorating one or more signs or symptoms of an ocular disease, disorder, or condition. In particular embodiments of the invention, "treat," "treating," and "treatment" refer to reducing or inhibiting the growth of new blood vessels in the cornea; reducing the progression of structural distortion of the cornea; reducing redness and/or inflammation in the eye; and reducing or eliminating white plaques associated with leukoplakia.

As used herein, the terms "prevent," "preventing," and "prevention" refer to administering a therapeutically effective amount of melanin, or an analog, precursor, or derivative thereof, before the onset of an ocular disease, disorder, or condition, such that the ocular disease, disorder, or condition is prevented altogether, time-delayed as to its occurrence, or still occurs, but to a lesser extent, than in the absence of administration of melanin, or an analog, precursor, or derivative thereof. In particular embodiments of the invention, "prevent," "preventing," and "prevention" refer to inhibiting or slowing the onset of development or progression of corneal angiogenesis or a corneal ectatic disease.

In one embodiment, the invention provides a method of treating or preventing an ocular disease, disorder, or condition in a subject comprising administering to an eye of the subject a composition comprising a therapeutically effective amount of melanin or a derivative, analog, or precursor thereof, such that the ocular disease, disorder, or condition is treated or prevented.

Any ocular disease, disorder, or condition can be treated or prevented by a method of the invention in view of the present disclosure. According to preferred embodiments of the invention, the ocular disease, disorder, or condition to be treated or prevented affects the structures that form the anterior segment of the eye (front of the eye), such as the cornea of the eye, including, but not limited to corneal angiogenesis and corneal ectatic diseases, such as corneal keratoconus; and corneal diseases and other diseases that affect the eyelids having an inflammatory, infectious, toxic, or degenerative etiology. Other preferred ocular diseases, disorders, and conditions to be treated or prevented include those affecting the conjunctiva, particularly, conjunctivitis; hyperemia; and leukoplakia.

According to embodiments of the invention, a composition can be administered to an eye of a subject by any method known in the art including, but not limited to, topical application and injection. Injection can be subconjunctival injection (i.e., under the conjunctiva) or intraocular injection. In a preferred embodiment, the composition is topically administered, e.g., by eye drops or by swabbing.

A composition for use in a method of the invention can be in any form suitable for application to the eye. Compositions suitable for injection include, but are not limited to, liquid compositions such as solutions and suspensions. Compositions suitable for topical application include, but are not limited to, solutions, suspensions, eye drops, spray formulations, gels, ointments, creams, and emulsions. In a preferred embodiment of the invention, the composition is a solution, and is more preferably an aqueous solution. An aqueous solution for use in a method according to the invention can be made by, for example, mixing melanin with water. Melanin and water can be mixed together to form a homogenous aqueous solution. In certain embodiments, an aqueous solution for use in a method of the invention contains only melanin and water.

In a preferred embodiment of the invention, the composition is formulated for topical application to the eye. In a particularly preferred embodiment of the invention, the composition is an aqueous solution that is topically administered as eye drops.

According to embodiments of the invention, the composition can be applied to any part of the eye, and is preferably applied to the affected portion of the eye, e.g., cornea, conjunctiva, eyelids, etc. For example, to treat a corneal disease, the composition is preferably applied to the cornea. As another illustrative example, in the case of poisons or other toxins affecting the eye that have deeply penetrated the eye, the composition can be applied by intraocular injection, such as into the anterior chamber or vitreous chamber of the eye.

The concentration of melanin, or an analog, precursor, or derivative thereof, in a composition applied to an eye of a subject in a method of the invention can range from about 1.5% to about 10.0% (w/v), such as about 1.5%, 2.0%, 3.0%, 4.0%, 5.0%, 6.0%, 7.0%, 8.0%, 9.0%, or 10.0% (w/v). In a preferred embodiment, the concentration of melanin, or an analog, derivative, or precursor thereof is 3% (w/v).

According to embodiments of the invention, a composition comprising a therapeutically effective amount of melanin can be administered once, or it can be administered more than once. For example, the composition can be administered once daily, twice daily, once every week, or once every month. In severe cases, the composition can be administered every fifteen minutes, and once an improvement is noticed, the time between applications can be increased to every half hour, every hour, or every two hours, etc., as needed. Also according to embodiments of the invention, a composition can be administered prior to the onset of an ocular disease, disorder, or condition in order to prevent the ocular disease, disorder, or condition, or after the onset of an ocular disease, disorder or condition in order to treat the ocular disease, disorder, or condition. Melanin is usually well tolerated. However, some side effects may occur, such as swelling, irritation, or inflammation of the eyelids, conjunctiva, or cornea, or subconjunctival bleeding.

According to embodiments of the invention, the therapeutically effective amount of melanin, or an analog, precursor, or derivative thereof in a composition, the amount of the composition administered, and the frequency of administration can all vary depending on a variety of factors, such as the ocular disease, disorder, or condition to be treated or prevented, the severity of the ocular disease, disorder, or condition, the age and health of the subject to be administered the composition, etc. It is well within the purview of one of ordinary skill in the art to optimize each of these parameters in order to achieve the desired clinical outcome in view of the present disclosure.

For example, in certain embodiments of the invention, about 50 μL to 500 μL, preferably 50 μL to 200 μL, and more preferably 150 μL to 200 μL of a composition comprising 1.5% (w/v) to 10% (w/v) of melanin or an analog, derivative, or precursor thereof is administered per application. In particular embodiments of the invention, between one and five drops (about 50 μL per drop) of the composition is administered per application, such as one drop, two drops, three drops, four drops, or five drops.

As an illustrative and non-limiting example of a dosing regimen that can be followed in the methods of the invention for treating an acute ocular disease, disorder, or condition in a subject, about 50 μL to 100 μL of a 3% aqueous solution of melanin can be administered every thirty minutes at the start of treatment. Depending on the severity of the condition, the frequency of administration of the aqueous melanin solution can be adjusted to once every hour, once every two hours, etc. As another illustrative example, about 50 μL, to 100 μL, of a 3% aqueous solution of melanin can be administered four to six times daily to treat a chronic ocular disease, disorder, or condition. The frequency of administration can again be adjusted depending on the severity of the condition.

In a particular embodiment, the invention provides a method of treating an ocular disease, disorder, or condition in a subject comprising topically administering to an eye of the subject in need of the treatment a composition comprising a therapeutically effective amount of melanin or an analog, derivative, or precursor thereof to treat the ocular disease, disorder, or condition.

In another particular embodiment, the invention provides a method of treating leukoplakia or hyperemia in a human subject comprising topically administering to an eye of the subject in need of the treatment an aqueous composition comprising a therapeutically effective amount of melanin. According to embodiments of the invention, the hyperemia can be primary or secondary hyperemia.

Without wishing to be bound by any theories, one possible explanation for the efficacy of melanin, and its derivatives, analogs, and precursors in treating ocular diseases, disorders, and conditions is that applying melanin to the eye enhances "human photosynthesis" in the eye. As explained above, melanin is believed to transform light energy into chemical energy, analogous to the process by which plants use the pigment chlorophyll to transform light energy into chemical energy during photosynthesis. By analogy, the conversion of light energy into chemical energy by melanin has been designated "human photosynthesis." Direct application of melanin to the eye is thus also thought to induce "human photosynthesis" in the eye, resulting in increased splitting and reformation of the water molecule, which results in an increased release of energy. The increased amount of energy made available to the surrounding cells is believed to fuel many important biological reactions that take place in the cell, such as those needed for cellular repair, etc.

Again without wishing to be bound by any theories, melanin is a relatively large biomolecule, which allows it to function as a chelating agent in certain circumstances. Thus, it is also believed that the ability of melanin to chelate or inactivate certain biological molecules and molecules of foreign origin that are often present in diseased tissue increases the purity of the tissue and improves the efficiency of water dissociation by melanin. This has the effect of further enhancing any beneficial therapeutic effects that result from increased "human photosynthesis."

This invention will be better understood by reference to the non-limiting examples that follow, but those skilled in the art will readily appreciate that the examples are only illustrative of the invention and are not to be construed as limiting the invention in any way.

EXAMPLES

Example 1: Topical Treatment of Leukoplakia and Hyperemia of the Eye with Melanin A male patient, aged 30, had a small white plaque growing on the surface of his right eye (leukoplakia) and hyperemia (redness) (see FIG. 1A). The leukoplakia was hypothesized to be the result of excessive sun exposure and chemicals. The patient was initially treated with topical cortisone drops, and the cortisone treatment continued for two months. However, no improvement was observed with the topical cortisone drops, and cortisone treatment was thus stopped due to a lack of improvement.

One month subsequent to stopping cortisone treatment, the patient underwent treatment with a 3% aqueous solution of melanin (w/v) that was topically applied in the form of eye drops. The aqueous solution was produced by mixing water and chemically synthesized melanin (synthetic melanin). The aqueous solution did not contain any other components. Three to four drops (about 50 µL per drop) of the 3% aqueous melanin solution were administered for each application, and the solution was applied four times per day at approximately six hour intervals. After approximately three and a half months of treatment with the topical melanin solution, a dramatic improvement was observed. The same dosing regimen was used over the entire course of the treatment. In particular, the redness due to hyperemia was greatly reduced, and the small white plaque indicative of leukoplakia was no longer detectable by visual observation (see FIG. 1B).

The results of the above experiment indicate that topical application of melanin to the eye is effective in the treatment of hyperemia of the eye, particularly in humans. The results of the above experiment also indicate that topical application of melanin to the eye is effective in the treatment of disorders affecting the surface of the eye, such as the conjunctiva, including leukoplakia, particularly in humans.

Example 2: Prevention of Corneal Angiogenesis and Corneal Ectasia by Topical Treatment with Melanin The efficacy of melanin in preventing ocular diseases, disorders, and conditions was demonstrated using a rat model of corneal angiogenesis and corneal ectatic diseases, such as corneal keratoconus. In the rat model, varying concentrations of phenol are applied to a cornea of a rat to induce corneal angiogenesis and/or corneal ectatic diseases. Typically, lower concentrations of phenol induce corneal angiogenesis as compared to the concentrations needed to induce corneal ectatic diseases, and particularly corneal keratoconus. See International Application No. PCT/IB2015/000822, which discloses animal models of corneal angiogenesis and corneal ectatic diseases, and methods of making such animal models.

More specifically, as described in International Application No. PCT/IB2015/000822, aqueous solutions of phenol having a concentration of 0.1 M, 0.5 M, 1.0 M, 3.0 M, 5.6 M, or 8.5 M were prepared by mixing phenol and water. The solutions were then sterilized by heating to 100° C. for 15 minutes. Then, 10 µL of the sterile phenol solution was topically applied to the center of the cornea of the right eye of a Wistar rat that was two months old. Five rats were treated for each concentration of phenol tested. The phenol solution was allowed to absorb into the eye, and was applied only once. Prior to application of the phenol solution, there were no visible blood vessels in the cornea. However, new blood vessels began to form in the cornea upon treatment with all concentrations of the phenol solution tested in at least one of the rats in each group one week after application of the aqueous phenol solution. At the higher concentrations of phenol tested (e.g., 3.0 M, 5.6 M, and 8.5 M), changes associated with corneal ectasia, particularly corneal keratoconus, were also observed in some of the rats. The results are summarized in Table 1 below.

TABLE 1

Induction of corneal angiogenesis and corneal keratoconus with phenol in rats.

| Phenol Concentration | Number of Rats Treated | Observation in Treated Eye (Number of Rats) | | |
|---|---|---|---|---|
| | | Angiogenesis | Corneal Keratoconus | No Change |
| 0.1M | 5 | 1 | 0 | 4 |
| 0.5M | 5 | 1 | 0 | 4 |
| 1.0M | 5 | 3 | 0 | 2 |
| 3.0M | 5 | 4 | 2 | 1 |
| 6.5M | 5 | 4 | 2 | 1 |
| 8.5M | 5 | 3 | 1 | 2 |

Additional experiments to test the efficacy of melanin in preventing ocular diseases, disorders, and conditions were subsequently designed based upon the above described observation that application of phenol to the eye induces corneal angiogenesis and/or corneal ectatic diseases. Aqueous solutions of phenol having a concentration of 0.1 M to 8.5 M phenol, including 0.1 M, 0.5 M, 1.0 M, 3.0 M, 6.5 M, and 8.5 M were prepared by mixing phenol and water. The solutions were then sterilized by heating to 100° C. for 15 minutes. Then, 10 µL of the phenol solution of the desired concentration was topically applied to the center of the cornea of only the right eye of five male Wistar rats (two months old) to induce corneal angiogenesis and/or corneal keratoconus. The phenol aqueous solution was allowed to absorb into the eye, and was applied only once. About five minutes after the application of phenol, 20 µL of a 3% (w/v) aqueous solution of melanin (prepared by mixing water and melanin) was topically applied to only the right eye of each of the rats. The aqueous solution of melanin was applied only once. All rats treated with phenol in the right eye were also treated with the aqueous melanin in the right eye. The left eye in each of the rats thus served as a control for the induction of spontaneous corneal angiogenesis and/or keratoconus.

Prior to application of the phenol solution and the aqueous melanin solution, there were no visible blood vessels in the cornea in either eye of the rats. One week following application, changes typically observed after the application of phenol, e.g., formation of new blood vessels and distortion of the cornea associated with corneal angiogenesis and corneal keratoconus, were not observed in the right eye of any of the rats, even though the right eye was treated with phenol. This was unexpected in view of the previous experiments demonstrating that application of phenol to the eyes of rats induces corneal angiogenesis and/or corneal ectatic diseases, as explained above.

The results of the above experiment indicate that topical application of melanin to the eye can be used to prevent ocular diseases, disorders, and conditions, such as corneal angiogenesis and corneal ectatic diseases, particularly in mammals.

Example 3: Subconjunctival Injection of Melanin

The effect of subconjunctival injection of melanin into the eyes of healthy rats was tested. Rats were put under general anesthesia by intraperitoneal injection of barbiturates. A total of five rats were used in the study. Then, 500 µL of a 3% aqueous melanin solution was administered to the right eye of each of the rats by subconjunctival injection. The left eye was left untreated.

Immediately after injection, the treated eyes exhibited an increase in size and some distortion due to the injection of the solution. However, twenty-four hours after the injection, no visible marks on the ocular tissue at the injection site were observed, nor were any visible signs of inflammation, irritation, or subconjunctival bleeding observed. These observed effects are similar to the observed effects of topical application of melanin to the cornea of healthy rats, except for the initial distortion caused by the injection.

These results of the above experiment demonstrate that the response of the conjunctiva to melanin injection is similar to the response of the cornea to topical application of melanin, suggesting that conjunctival diseases can also be effectively treated with topical application of melanin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

I claim:

1. A method of treating an ocular disease, disorder, or condition in a subject, the method comprising administering to an eye of the subject a composition comprising a therapeutically effective amount of melanin, to treat the ocular disease, disorder, or condition, wherein the ocular disease, disorder, or condition is selected from the group consisting of leukoplakia, hyperemia, and inflammation of the eyelids.

2. The method according to claim 1, wherein the composition is administered topically or by injection.

3. The method according to claim 1, wherein the composition comprises synthetic melanin or natural melanin.

4. The method according to claim 1, wherein the composition is a topical composition selected from the group consisting of a solution, suspension, eye drops, spray formulation, ointment, gel, cream, and emulsion.

5. The method according to claim 1, wherein the composition is an aqueous solution.

6. The method according to claim 1, wherein the composition is administered as eye drops.

7. The method according to claim 1, wherein the composition comprises 1.5% to 10% (w/v) of melanin.

8. The method according to claim 1, wherein the subject is a human.

9. A method of treating an ocular disease, disorder, or condition in a subject, the method comprising topically administering to an eye of the subject in need of the treatment a composition comprising a therapeutically effective amount of melanin to treat the ocular disease, disorder, or condition, wherein the ocular disease, disorder, or condition is selected from the group consisting of leukoplakia, hyperemia, and inflammation of the eyelids.

10. The method according to claim 9, wherein the composition comprises 1.5% to 10% (w/v) of melanin.

11. The method according to claim 9, wherein the composition is administered as eye drops.

12. The method according to claim 9, wherein the composition comprises natural melanin or synthetic melanin.

13. A method of treating leukoplakia or hyperemia in a human subject, the method comprising topically administering to an eye of the subject in need of the treatment an aqueous composition comprising a therapeutically effective amount of melanin to treat leukoplakia or hyperemia.

14. The method according to claim 13, wherein the aqueous composition is administered as eye drops.

15. The method according to claim 13, wherein the aqueous composition comprises 1.5% to 10% (w/v) of melanin.

16. The method according to claim 9, wherein the composition administered is selected from the group consisting of a solution, suspension, eye drops, spray formulation, ointment, gel, cream and emulsion.

17. The method according to claim 9, wherein the subject is a human.

18. The method according to claim 1, wherein the ocular disease, disorder, or condition is hyperemia or leukoplakia.

19. The method according to claim 9, wherein the ocular disease, disorder, or condition is hyperemia or leukoplakia.

* * * * *